(12) United States Patent
Hilfenhaus et al.

(10) Patent No.: US 8,383,527 B2
(45) Date of Patent: Feb. 26, 2013

(54) ANTIMICROBIAL COMPOSITE

(75) Inventors: Peter Hilfenhaus, Hamburg (DE);
Heike John, Neu Wulmstorf (DE);
Harald Büttner, Neu Wulmstorf (DE)

(73) Assignee: Beiersdorf AG, Hamburg (DE)

( * ) Notice: Subject to any disclaimer, the term of this patent is extended or adjusted under 35 U.S.C. 154(b) by 0 days.

(21) Appl. No.: 12/232,699

(22) Filed: Sep. 23, 2008

(65) Prior Publication Data

US 2009/0092788 A1   Apr. 9, 2009

Related U.S. Application Data

(63) Continuation of application No. 10/654,949, filed on Sep. 5, 2003, now abandoned.

(30) Foreign Application Priority Data

Jun. 23, 2003   (DE) .................................. 103 28 261

(51) Int. Cl.
*B32B 5/02* (2006.01)
*A61F 13/00* (2006.01)

(52) U.S. Cl. .................. 442/123; 442/1; 442/2; 442/58; 424/443; 424/445; 424/447; 602/42; 602/48

(58) Field of Classification Search .................. 424/618, 424/404, 445, 446, 447, 443; 442/38, 123, 442/43, 46, 49, 41, 394, 1, 2, 58; 602/42, 602/48
See application file for complete search history.

(56) References Cited

U.S. PATENT DOCUMENTS

| | | | |
|---|---|---|---|
| 2,934,066 A | 4/1960 | Stowasser | |
| 4,661,099 A | 4/1987 | Bittera et al. | |
| 4,767,401 A * | 8/1988 | Seiderman | 604/20 |
| 4,817,594 A | 4/1989 | Juhasz | |
| 4,997,425 A | 3/1991 | Shioya et al. | |
| 5,087,686 A | 2/1992 | Ansell et al. | |
| 5,147,338 A | 9/1992 | Lang et al. | |
| 5,328,450 A | 7/1994 | Smith et al. | |
| 5,395,305 A | 3/1995 | Koide et al. | |
| 5,429,591 A | 7/1995 | Yamamoto et al. | |
| 5,445,604 A | 8/1995 | Lang | |
| 5,454,886 A | 10/1995 | Burrell et al. | |
| 5,584,801 A | 12/1996 | Kuroyanagi et al. | |
| 5,681,575 A | 10/1997 | Burrell et al. | |
| 5,681,579 A | 10/1997 | Freeman et al. | |
| 5,747,178 A | 5/1998 | Sodervall et al. | |
| 5,753,251 A | 5/1998 | Burrell et al. | |
| 5,770,255 A | 6/1998 | Burrell et al. | |

(Continued)

FOREIGN PATENT DOCUMENTS

| CA | 2 438 765 | 8/2002 |
|---|---|---|
| DE | 517 105 | 1/1931 |

(Continued)

OTHER PUBLICATIONS http://www.nanocrystallinesilver.org, Copyright 2002, Parts 1-5.

(Continued)

*Primary Examiner* — Matthew Matzek
(74) *Attorney, Agent, or Firm* — Abel Law Group, LLP

(57) ABSTRACT

An antimicrobial composite which comprises a first, liquid-permeable layer which is substantially completely bonded to a second liquid-absorbing layer. The first layer comprises a coating of at least one antimicrobial metal as such on the side which is bonded to the second layer. Substantially no antimicrobial metal in elemental form is present on exterior surfaces of the composite.

20 Claims, 2 Drawing Sheets

U.S. PATENT DOCUMENTS

| | | | |
|---|---|---|---|
| 5,782,788 A | 7/1998 | Widemire | |
| 5,837,275 A | 11/1998 | Burrell et al. | |
| 5,844,013 A | 12/1998 | Kenndoff et al. | |
| 5,849,311 A | 12/1998 | Sawan et al. | |
| 5,958,440 A | 9/1999 | Burrell et al. | |
| 5,973,221 A | 10/1999 | Collyer et al. | |
| 5,985,301 A | 11/1999 | Nakamura et al. | |
| 5,985,308 A | 11/1999 | Burrell et al. | |
| 6,017,553 A | 1/2000 | Burrell et al. | |
| 6,066,773 A | 5/2000 | Freeman et al. | |
| 6,087,549 A | 7/2000 | Flick | |
| 6,113,636 A | 9/2000 | Ogle | |
| 6,153,215 A | 11/2000 | Samuelsen et al. | |
| 6,168,800 B1 * | 1/2001 | Dobos et al. | 424/405 |
| 6,187,290 B1 | 2/2001 | Gilchrist et al. | |
| 6,190,407 B1 | 2/2001 | Ogle et al. | |
| 6,224,898 B1 | 5/2001 | Balogh et al. | |
| 6,238,686 B1 | 5/2001 | Burrell et al. | |
| 6,267,782 B1 | 7/2001 | Ogle et al. | |
| 6,322,588 B1 | 11/2001 | Ogle et al. | |
| 6,333,093 B1 | 12/2001 | Burrell et al. | |
| 6,399,091 B1 | 6/2002 | Berthold et al. | |
| 6,482,444 B1 | 11/2002 | Bellantone et al. | |
| 6,485,735 B1 | 11/2002 | Steen et al. | |
| 6,530,951 B1 | 3/2003 | Bates et al. | |
| 6,555,599 B2 | 4/2003 | Lever et al. | |
| 6,565,913 B2 | 5/2003 | Arps et al. | |
| 6,582,715 B1 | 6/2003 | Barry et al. | |
| 6,592,888 B1 | 7/2003 | Jensen et al. | |
| 6,593,260 B2 | 7/2003 | Nomura | |
| 6,903,243 B1 | 6/2005 | Burton | |
| 2001/0006987 A1 | 7/2001 | Nomura | |
| 2001/0009831 A1 | 7/2001 | Schink et al. | |
| 2001/0023156 A1 | 9/2001 | Nomura | |
| 2002/0051824 A1 | 5/2002 | Burrell et al. | |
| 2002/0156411 A1 | 10/2002 | Ahrens et al. | |
| 2002/0160037 A1 | 10/2002 | Ahrens et al. | |
| 2002/0182265 A1 | 12/2002 | Burrell et al. | |
| 2002/0192298 A1 | 12/2002 | Burrell et al. | |
| 2003/0021854 A1 | 1/2003 | Burrell et al. | |
| 2003/0054046 A1 * | 3/2003 | Burrell et al. | 424/618 |
| 2003/0054646 A1 | 3/2003 | Burrell et al. | |
| 2003/0072810 A1 | 4/2003 | Burrell et al. | |
| 2003/0086977 A1 | 5/2003 | Gillis | |
| 2003/0099718 A1 | 5/2003 | Burrell et al. | |
| 2003/0170314 A1 | 9/2003 | Burrell et al. | |
| 2003/0180378 A1 | 9/2003 | Gillis et al. | |
| 2003/0180379 A1 | 9/2003 | Burrell et al. | |
| 2003/0185901 A1 | 10/2003 | Burrell et al. | |
| 2003/0194444 A1 | 10/2003 | Burrell et al. | |
| 2003/0203046 A1 | 10/2003 | Burrell et al. | |
| 2003/0206966 A1 | 11/2003 | Burrell et al. | |
| 2004/0002416 A1 | 1/2004 | Nomura | |
| 2004/0002417 A1 | 1/2004 | Nomura | |
| 2004/0241214 A1 | 12/2004 | Kirkwood et al. | |
| 2006/0057369 A1 | 3/2006 | Hilfenhaus et al. | |
| 2006/0057914 A1 | 3/2006 | Hilfenhaus et al. | |

FOREIGN PATENT DOCUMENTS

| | | |
|---|---|---|
| DE | 529 559 | 7/1931 |
| DE | 547 046 | 3/1932 |
| DE | 31 11 336 | 4/1982 |
| DE | 32 28 851 | 2/1984 |
| DE | 199 58 458 | 6/2001 |
| DE | 101 08 083 | 9/2002 |
| EP | 0 099 758 | 2/1984 |
| EP | 0 475 807 | 3/1992 |
| EP | 1 116 698 | 7/2001 |
| EP | 1 116 700 | 7/2001 |
| GB | 1 395 815 | 5/1975 |
| GB | 2 074 029 | 10/1991 |
| WO | 98/41095 | 9/1998 |
| WO | 00/25726 | 5/2000 |
| WO | 01/60599 | 8/2001 |
| WO | 02/09729 | 2/2002 |

OTHER PUBLICATIONS

Hospital Pharmacist, Oct. 2002, vol. 9, pp. 261-266.

Nielsen, B., et al., "Antibacterial activity of silver containing dressings", presented at the 12th Conference of the European Wound Management Association May 2002.

EWMA Journal 2003, vol. 3, No. 1, pp. 17-19.

http://www.silverlom.com/compare.htm, Acticoat® Comparison; Copyright 1998-2001 Argentum Medical, LLC.

Muller et al., "Antibacterial activity and endotoxin-binding capacity of Actisorb® Silver 220", Journal of Hospital Infection (2003) 53: 211-214.

Actisorb Silver 222, from internet website www.dressings.org/Dressings/actisorb-silver.html, 5 pages, dated Mar. 28, 2002.

* cited by examiner

A         B         C

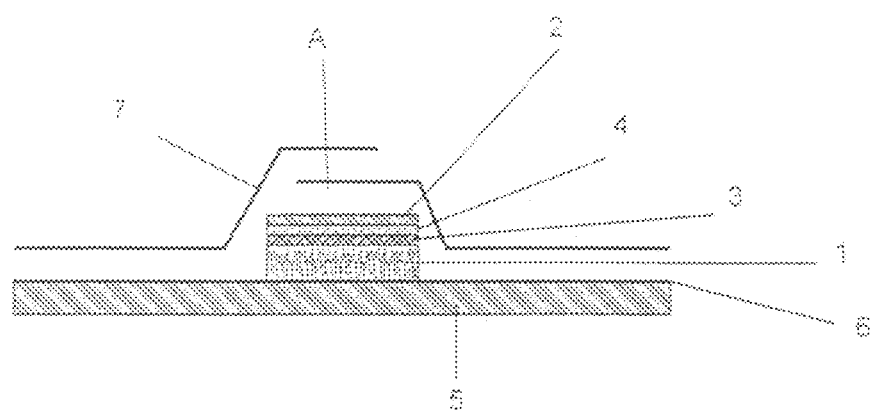
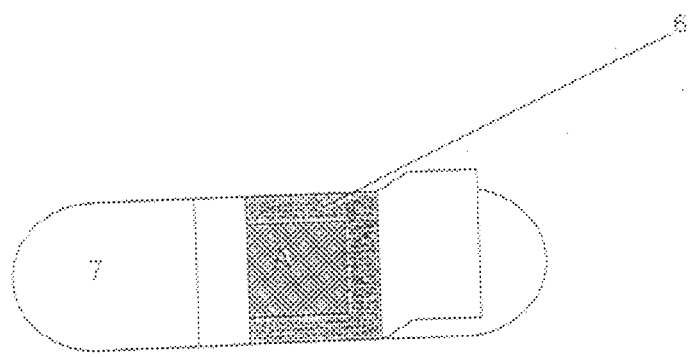

ANTIMICROBIAL COMPOSITE

CROSS-REFERENCE TO RELATED APPLICATIONS

The present application is a continuation of U.S. application Ser. No. 10/654,949, filed Sep. 5, 2003, now abandoned which claims priority under 35 U.S.C. §119 of German Patent Application No. 103 28 261.0, filed Jun. 23, 2003. The disclosures of these applications are expressly incorporated by reference herein in their entireties.

BACKGROUND OF THE INVENTION

1. Field of the Invention

The present invention relates to antimicrobial composites which may be used, in particular, as wound coverings, dressings, cloths, and the like. By coating one side of a liquid-permeable material with an antimicrobial metal such as silver and laminating the resultant material to a material such as a liquid-absorbing nonwoven material with the metal coating facing the liquid-absorbing material, the abrasion of metal particles may be prevented while at the same time, the antimicrobial and disinfectant effect of the metal coating is retained.

2. Discussion of Background Information

Treating and healing bacterially contaminated skin and wounds, or infected skin and wounds is a major challenge to medicine and the natural sciences. Poorly healing and chronic wounds frequently become populated by a wide variety of microorganisms that considerably delay healing and sometimes even prevent healing altogether. Frequently, in the case of acute wounds that are caused by trauma, surgical intervention or even just simple injury, the penetration and infection by pathogenic microorganisms can, however, not completely be prevented.

Various possibilities are described for removing microorganisms from the contaminated or infected tissue of a wound and/or for killing the microorganisms. In addition to the oral administration of antibiotics, the removal of pathogenic microorganisms from a wound may be achieved, in accordance with the prior art, by the topical application of a disinfectant or an antibiotic. However, antiseptics and antibiotics are cytotoxic; in addition, many pathogenic strains have developed resistances to antibiotics.

An example of the known antimicrobial and/or prophylactic treatment of contaminated or infected wounds is the use of oxidants such as tincture of iodine, or of antiseptics such as ointments which contain silver sulfadiazine.

For a very long time, silver has been the agent of choice for treating infections, due to its broad bactericidal and fungicidal effect. In addition to its broad range of activity, silver is effective in minute, i.e., trace amounts (oligodynamic effect). Since the amounts of silver are so small, the tolerance is excellent. For example, silver aerosols, silver-containing solutions, ointments or tablets, etc. are widely used as antiseptics.

Silver-containing products are also used in the form of corresponding antimicrobially treated or impregnated wound dressings and wound care materials. The use of silver-containing zeolites, glasses and zirconyl phosphates, and also of silver in elemental or nanocrystalline form, is known as well.

Basically, there are two forms used for the administration of silver (ions), i.e., forms in which the silver ions are present in the product per se, and forms in which the ionic form of silver is generated by the oxidation of elemental silver. The first case essentially involves a dissolution or ion-exchange process. This makes the silver ions rapidly available, but the amount of silver ions in the preparation drops quickly as well. To provide a sufficient amount of silver to counteract this disadvantage is not without problems. For example, the cytotoxicity of silver ions limits the maximum acceptable amount thereof that can be used in a product.

Another disadvantage is that silver is deactivated by proteins, other complex-formers, or in the presence of ions that form scarcely-soluble silver salts. These conditions doubtlessly exist in wound fluids. In contrast, the release of silver from "elemental" silver (silver metal) is slower and occurs over a longer period, but takes place continuously. Accordingly, a sufficient amount of silver ions that is harmless to the user can always be released from the reservoir of elemental silver, the amount of silver ions depending on whether more or less of these ions can be released by equilibrium processes. The release of silver is, therefore, "as needed," and the release of an effective quantity of silver is ensured.

An overview of known antimicrobial, silver-containing wound care materials is given in DE-A1-19958458.

A commercially available wound care product with antimicrobial properties is known under the name of Arglaes®. Its mode of action is based on "slow-release polymer" technology that causes a slow but constant release of silver ions in the moist milieu of the wound (*Biomed. Mat.*, November 1995; *Health Industry Today,* 1 Nov. 1997, Vol. 58, No. 11).

DE-A1-19958458 discloses wound coverings comprising a synthetic polymer material which contains metal ion-containing zeolites.

Silver-containing glasses that have an antimicrobial effect are known from EP-A1-1116698 and EP-A1-1116700. These glasses are embedded in thermoplastic polymers that are used in a wide variety of forms for household and hygienic applications such as wallpaper, cutting boards, etc.

U.S. Pat. Nos. 5,753,251 and 5,681,575 describe antimicrobial coatings with so-called nanocrystalline silver that are formed on a medical product by depositing metals such as, e.g., silver from a gas phase. The antimicrobial effect is based on the release of ions, atoms, molecules or clusters from a disordered metal lattice when the silver is in contact with water or alcohol-based electrolytes. The corresponding product is known under the name Acticoat®. One of the disadvantages of this product is the visibly identifiable silver abrasion that causes a black discoloration of the covered skin area.

U.S. Pat. No. 2,934,066 describes a wound covering coated with metals, especially silver, which is reported to have a disinfecting effect.

The entire disclosures of the documents cited above, as well as those of all other documents mentioned in the present specification, are expressly incorporated by reference herein as if each of these documents in its entirety were part of the present specification.

Wound coverings comprising a non-woven material that is covered with a silver-coated polyethylene mesh are also known, e.g., Katomed®.

In all of the known disinfectant wound dressings which comprise a coating of elemental or nanocrystalline silver, the silver coating is intended to directly contact the wound. A disadvantage of these disinfecting materials is, therefore, that upon their contacting of the skin or wound they give rise to an abrasion and release of small particles of elemental silver. These particles form inclusions in the skin or wound, so-called granulomas, and can lead to complications during wound healing. Furthermore, due to the generated black discoloration, the aesthetic acceptance of corresponding products among users is very low.

It would be desirable to have available a material, e.g., a skin or wound dressing, which does not show the disadvantages of the known materials, but nevertheless shows antimicrobial activity.

SUMMARY OF THE INVENTION

The present invention provides an antimicrobial composite comprising a first, liquid-permeable layer and a second layer arranged on the first layer. An antimicrobial metal in elemental form is present between these layers. Moreover, substantially none of this antimicrobial metal in elemental form is present on exterior surfaces of the composite.

In one aspect of the composite, the first layer may comprise a foramenous structure, and preferably comprises a hole structure and/or a mesh structure. For example, the first layer may comprise a perforated film and/or a mesh.

In another aspect of the composite, the first layer may comprise an organic polymer, preferably, a polyolefin such as, e.g., polyethylene and/or polypropylene In yet another aspect, the first layer may comprise a polyethylene mesh.

In a still further aspect, the first layer preferably comprises openings having a size of from about 250 μm to about 1400 μm, e.g., from about 400 μm to about 700 μm. In one embodiment, the openings may have a substantially triangular shape and/or may provide an open area of from about 15% to about 60% of the surface area of the first layer.

In another aspect of the composite, the first layer may have a thickness of from about 0.02 mm to about 0.8 mm, e.g., of from about 0.05 mm to about 0.5 mm.

In a still further aspect, the second layer is a liquid-permeable layer or a liquid-absorbing layer.

In another aspect, the second layer may comprise a perforated film and/or a mesh.

In yet another aspect, the second layer may comprise an organic polymer. The organic polymer may comprise a polyolefin. For example, the second layer may comprise a polyethylene mesh.

In a still further aspect of the composite of the present invention, the second layer preferably has a thickness of from about 0.02 mm to about 2.5 mm.

In another aspect, the second layer may be a liquid-absorbing layer. This layer may have a liquid-absorbing capacity of from about 300 g/m$^2$ to about 2000 g/m$^2$, e.g., from about 400 g/m$^2$ to about 1000 g/m$^2$. For example, the liquid-absorbing layer may comprise a textile sheet, which textile sheet may in turn comprise a nonwoven, a fleece, a woven fabric, a knit and/or a felt.

In a still further aspect, the second layer may comprise fibers and/or yarns.

In another aspect, the second layer may comprises viscose, polyolefin (e.g., polyethylene and/or polypropylene) and/or polyester.

In another aspect of the composite, the second layer preferably has a thickness of from about 0.3 mm to about 2.4 mm, e.g., from about 0.5 mm to about 1.4 mm and/or an area weight of from about 80 g/m$^2$ to about 200 g/m$^2$.

In a still further aspect, the second layer may comprise a superabsorber, for example, a superabsorber comprising a polymer having recurring units derived from acrylic acid and derivatives thereof. The superabsorber may be present in an amount of from about 0.01% to about 40% by weight, based on the weight of the second layer.

In another aspect of the composite of the present invention, the antimicrobial metal preferably comprises at least one of Ag, Au, Pd, Pt, Cu, Ir, Zn, Sn, Sb, Bi and/or an alloy comprising one or more of these metals. Preferably, the antimicrobial metal comprises Ag and/or an alloy thereof.

In yet another aspect of the present composite, the antimicrobial metal may be provided as a coating on at least one of the surfaces of the first and second layers.

In another aspect of the composite, the antimicrobial metal may be present as a layer which comprises the antimicrobial metal and is arranged between the first and second layers.

In a still further aspect, the composite preferably has a sheet-like (web-like) structure.

In yet another aspect of the composite of the present invention, the antimicrobial metal (e.g., silver) preferably is present in an amount of from about 1 mg/m$^2$ to about 1 g/m$^2$ of composite, e.g., in an amount of from about 10 mg/m to about 600 mg/m$^2$ of composite, more preferably in an amount of from about 50 mg/m$^2$ to about 450 mg/m$^2$ of composite, e.g., in an amount of from about 60 mg/m$^2$ to about 80 mg/m$^2$ of the composite.

In another aspect of the composite of the present invention, the first layer has a silver coating on the side (surface) thereof which faces the second layer and/or the second layer has a silver coating on the side (surface) thereof which faces the first layer. In yet another aspect, an intermediate layer is arranged between the silver coating and the first layer. The intermediate layer preferably comprises aluminum.

In yet another aspect of the composite, the composite preferably has an area weight of from about 50 g/m$^2$ to about 300 g/m$^2$, e.g., from about 80 g/m$^2$ to about 160 g/m$^2$, and/or a thickness of from about 0.4 mm to about 2.5 mm, e.g., from about 0.5 mm to about 1.4 mm, and/or a peeling strength of from about 0.05 N/cm to about 1.5 N/cm, e.g., from about 0.15 N/cm to about 0.8 N/cm, and/or a maximum tensile strength of from about 10 N/cm to about 40 N/cm, and/or a 24-hour release of the antimicrobial metal (e.g., silver) of from about 0.05 mg/m$^2$ to about 3 mg/m$^2$ of composite, e.g., of from about 0.1 mg/m$^2$ to about 2 mg/m$^2$ of composite and/or a size of at least about 0.5 cm$^2$ and/or a size of not higher than about 1 m$^2$.

The present invention also provides a wound covering article, a skin care article and a diaper, all of which comprise the above composite, including all of the various aspects thereof.

The wound covering article, for example, may further comprise a backing material arranged on the second layer of the composite. The backing material may carry an adhesive, e.g., a UV-curable acrylic adhesive or a rubber-based hot melt adhesive, on the side thereof which faces the second layer. Furthermore, the backing material preferably comprises a polyester nonwoven and/or a polyethylene film.

The present invention also provides a method of covering a wound. The method comprises placing the above wound covering article, including the various aspects thereof, on the wound so that the first layer of the composite contacts the wound.

The present invention also provides a method of covering a wound. The method comprises providing a material which comprises a liquid-permeable layer and an antimicrobial metal in elemental form associated with this layer (e.g., coated with the metal and/or having the metal incorporated therein and/or being in (direct) contact with the metal, etc.), and placing the material on the wound so that a surface of the liquid-permeable layer which is substantially free of the antimicrobial metal in elemental form contacts the wound.

In one aspect of the method, the liquid-permeable layer preferably comprises a foramenous material, e.g., a hole and/ or a mesh structure. For example, the liquid-permeable layer may comprise a perforated film and/or a mesh, e.g., a polyolefin mesh.

The present invention also provides a process of making an antimicrobial composite as set forth above. The process comprises bonding together a first, liquid-permeable material and a second material which is liquid-permeable and/or liquid-absorbing. At least one of the first and second materials is coated with an antimicrobial metal in elemental form on a side (surface) thereof which faces the other material, whereas substantially no antimicrobial metal in elemental form is present on the exterior surface of the composite.

In one aspect, the process may comprise providing a liquid-permeable, sheet-like material, coating one side of the material with the antimicrobial metal and bonding a liquid-absorbing material to that side of the liquid-permeable material which has the antimicrobial metal thereon. The liquid-permeable material preferably comprises a hole and/or a mesh structure. In another aspect of the process, the liquid-permeable material may be coated with the metal by a technique which comprises vapor deposition, e.g., by vacuum evaporation, sputtering, ion-beam assisted deposition, ion plating or magnetron sputtering.

In another aspect of the process of the present invention, the liquid-permeable material has an intermediate coating on that side thereof which is to be coated with the antimicrobial metal. The intermediate coating preferably comprises aluminum in metallic form.

In a still further aspect of the present process, the liquid-absorbing material and the liquid-permeable material are bonded to each other by lamination under heat and/or pressure, gluing, welding, and/or sewing.

As mentioned above, the first layer of the composite of the present invention is a liquid-permeable layer. The term "liquid-permeable" as used in the present specification and the appended claims is interchangeable with the term "fluid-permeable" and denotes a material which is capable of allowing liquid (fluid) such as water, wound secretions (wound exudate) etc., present on one side of the material to get to the opposite side of the material, irrespective of the way and/or mechanism through which this is accomplished. Accordingly, any material which is not completely impervious to liquid (fluid) is "liquid-permeable" for the purposes of the present invention. In this regard, it should be noted that a liquid-absorbing material may become liquid-permeable once the liquid absorbing capacity of the material is exceeded. Preferably, the liquid-permeable material has a foramenous structure, e.g., a hole or mesh structure. Non-limiting examples of corresponding materials are a perforated film and a mesh.

The material of the first layer will usually comprise one or more substantially bioinert materials, e.g., a (natural, semi-synthetic or synthetic) organic polymer, preferably, a polyolefin such as, e.g., polyethylene and/or polypropylene. However, materials different from organic polymers may be used as well, as long as they can be made to be—or already are—liquid-permeable. If the composite of the present invention is to be used in wound-care applications, the material is preferably substantially non-adhering to the wound.

Particularly in cases where the liquid-permeable material comprises a net, the openings thereof preferably have an (average) size (=length of the longest bisector) of at least about 250 µm, e.g., at least about 400 µm, and not higher than to about 1400 µm, e.g., not higher than about 1000 µm, or not higher than about 700 µm. The openings may be of any shape such as, e.g., circular, triangular, rectangular, etc., and different shapes and/or different sizes of openings may be present in the same material. Preferably, the open area created by these openings is at least about 15%, e.g., at least about 25%, and not more than about 60%, e.g., not more than about 50%, of the surface area of the first layer. The same applies to other liquid-permeable structures such as, e.g., perforated films, although in this case the size of the hole openings may be by far larger than those usually encountered with a net structure (e.g., up to about 3 mm or even larger). Holes may be created (e.g., in a film) by many different techniques, e.g., by mechanical perforation, punching, embossing, flame-perforation, etc. Moreover, holes may be present in the material from the beginning, e.g., in the case of nonwovens (e.g., spun bonded nonwovens), and woven or knitted fabrics.

The first layer will usually have a thickness of at least about 0.02 mm, e.g., at least about 0.05 mm, or at least about 0.1 mm. Usually the thickness of the first layer will be not higher than about 0.8 mm, e.g., not higher than about 0.5 mm, or not higher than about 0.3 mm. It should be noted that while it is currently preferred for the first layer to be composed of a single layer, the first layer of the composite of the present invention may itself be a composite of two or more individual layers (e.g., a combination of a perforated film and a mesh), in which case the above thickness values refer to the entire first layer. The unit area weight of the first layer, including any antimicrobial metal which may be combined therewith (in particular, silver), preferably is in the range of from about 10 $g/m^2$ to about 40 $g/m^2$, e.g., about 25 $g/m^2$ (as determined by DIN EN 29073-1).

It should also be noted that the first layer of the composite of the present invention may have a variety of substances on the surface thereof which is to contact the wound, provided these substances do not interfere to any significant extent with the liquid-permeability of the layer and the antimicrobial effect exerted by the metal. Non-limiting examples of such substances are compounds and compositions which promote wound healing and/or have a skin care effect.

Non-limiting examples of preferred materials for use in or as the first layer of the composite of the present invention are polyethylene nets available under the trade name Delnet® (Applied Extrusion Technologies, Wilmington, Del.). These nets are produced by extrusion, embossing and stretching of films. A huge variety of these nets is commercially available and may be produced by altering the polymer blend, the melt temperature, the embossing pattern, and the stretch ratio.

The second layer of the composite of the present invention will usually be liquid-absorbing, or at least liquid-permeable. Where the second-layer is (merely) liquid-permeable, the second layer may be the same as, or similar to the first layer, and in this case the above comments with respect to the first layer may be referred to with respect to properties, structure, etc. of the second layer.

The second layer of the composite of the present invention preferably is a liquid-absorbing layer. The term "liquid-absorbing" as used in the present specification and in the appended claims denotes a material which is capable of not only taking up a certain amount of liquid (fluid), but also of retaining the liquid within its structure under atmospheric pressure. Usually, a liquid-absorbing material will be capable of retaining an amount of liquid which equals at least about 5%, preferably at least about 10% of its own weight.

The liquid-absorbing capacity of the preferred liquid-absorbing second layer of the composite of the present invention (determined according to DIN 53923) will usually be at least about 300 $g/m^2$, e.g., at least about 400 $g/m^2$, or at least about 500 $g/m^2$, but will usually not be higher than about 2000 $g/m^2$, e.g., not higher than about 1500 $g/m^2$, not higher than about 1000 $g/m^2$, or not higher than about 800 $g/m^2$. However, higher liquid-absorbing capacities than those given above may be more appropriate in certain cases, for example, for compresses for use with larger wounds.

Where the second layer is liquid-absorbing, the second layer may be composed of any material that is liquid-absorbing and is compatible with the intended use of the composite. Preferably, the liquid-absorbing material will be substantially bioinert. For example, the second layer may comprise a textile sheet and/or a foam, e.g., a polyurethane foam. The textile sheet may comprise, by way of non-limiting example, a nonwoven, a fleece, a woven fabric, a knit and/or a felt. Preferred examples of the liquid-absorbing material include nonwovens, e.g., nonwovens which are bonded by various technologies such as, e.g., thermal bonding, stitch-bonding (Malivlies, Maliwatt), carding, spun-lacing, melt blowing, etc.

By way of non-limiting example, the second layer may comprise one or more natural, semisynthetic and/or synthetic materials such as, e.g., viscose, cellulose and derivatives thereof, polyolefins (e.g., polyethylene and/or polypropylene), polyesters, polyetheresters, polyamides, polyurethanes, hydrocolloids, hydrogels, and in general, materials which are conventionally used for making wound coverings/dressings.

The second layer of the composite of the present invention preferably has a thickness of at least about 0.3 mm, e.g., at least about 0.4 mm, or at least about 0.5 mm. The thickness will usually be not higher than about 2.4 mm, e.g., not higher than about 2.0 mm, or not higher than about 1.4 mm. Like in the case of the first layer, the second layer of the composite of the present invention may itself be a composite of two or more individual layers (by way of non-limiting example, a combination of two layers or sheets of different liquid-absorbing materials such as, e.g., a foam and a textile sheet), in which case the above values (and those given below) refer to the entire second layer.

The desirable area weight of the second layer of the composite of the present invention depends on the intended use and the type of lamination. For standard bandage products for treating conventional wounds the area weight of the second, liquid-absorbing layer (e.g., the nonwoven), as determined according to DIN EN 29073, will usually be not lower than about 80 g/m$^2$, e.g., not lower than about 100 g/m$^2$, and be not higher than about 200 g/m$^2$, e.g., not higher than about 150 g/m$^2$, or not higher than about 130 g/m$^2$. An area weight of about 125 g/m$^2$ is particularly preferred. In certain cases higher area weights than those indicated above may be more appropriate, for example, for compresses for use with larger wounds.

Additionally, the second (liquid-absorbing) layer may comprise one or more superabsorbers such as, for example, water-insoluble, cross-linked polymers that can swell and form hydrogels to absorb and store large amounts of liquid (e.g., water), even under pressure. A non-limiting example of a suitable superabsorber is a polymer which comprises recurring units derived from acrylic acid and derivatives thereof. When present at all, the superabsorber(s) will usually be present in an amount of from about 0.01% to about 40% by weight, based on the weight of the second layer.

The composite of the present invention comprises one or more antimicrobial metals such as, e.g., Ag, Au, Pd, Pt, Cu, Ir, Zn, Sn, Sb, Bi, and alloys comprising one or more of these metals. A particularly preferred metal is silver. The term "antimicrobial" as used in the present specification and the appended claims is to be understood in its broadest sense, and is inclusive of terms like "disinfectant", "antibacterial", "antifungal" etc. In particular, "antimicrobial" denotes activity against pathogenic microorganisms of any kind.

The antimicrobial metal in elemental form may be present between the first and second layers of the composite of the present invention in any form which ensures that metal (ions) will be present on the external surface of the first layer (opposite the surface that faces the second layer) when this surface is contacted with (aqueous) liquid (water, liquid electrolyte, wound exudate etc.) for a sufficient period of time. Accordingly, the expression "present between the first and second layers" as used in the present specification and the appended claims does not exclude, but rather includes, composites in which the antimicrobial metal is present within the first layer and/or within the second layer instead of, or in addition to, its presence between the layers. By way of non-limiting example, the first layer of the composite of the present invention may be composed of a combination of two individual liquid-permeable layers (e.g., a mesh and a perforated film or two perforated films), and the antimicrobial metal may be sandwiched between (e.g., be present at the interface of) these two individual layers. Thus, the present invention encompasses any composite wherein the antimicrobial metal in elemental form is present within the composite, but substantially no antimicrobial metal in elemental form is present on exterior surfaces of the composite. "Substantially no antimicrobial metal in elemental form is present on exterior surfaces of the composite" means that no more than trace amounts of antimicrobial metal, in particular, amounts which by themselves will not give rise to a noticeable antimicrobial effect, are present on exterior surfaces of the composite.

In a preferred embodiment of the composite of the present invention, the antimicrobial metal is present as a coating on at least one of the surfaces of the first and second layers, preferably (at least) on one of the surfaces of the first layer, although a corresponding coating or the like may also be present on one or both sides of the second layer.

The antimicrobial metal may be present as such (i.e., without any other materials), but it may also be present in any other suitable form, for example, as a layer which comprises the antimicrobial metal and other materials such as, e.g., in the form of a porous polymer matrix which contains embedded antimicrobial metal.

The antimicrobial metal (e.g., silver) will usually be present in an amount of at least about 1 mg/m$^2$, e.g., at least about 10 mg/m$^2$, at least about 50 mg/m$^2$, at least about 60 mg/m$^2$, or at least about 70 mg/m$^2$. Usually the amount of silver will not be higher than about 1 g/m$^2$, e.g., not higher about 600 mg/m$^2$, not higher than about 450 mg/m$^2$, not higher than about 200 mg/m$^2$, or not higher than about 80 mg/m$^2$ of the composite.

One or more other layers may be arranged between the antimicrobial metal and the first layer and/or the second layer. For example, an intermediate layer may be arranged on the surface of the first layer (and/or the second layer) onto which the antimicrobial metal is to be applied. The intermediate layer may serve various purposes, e.g., to provide a higher optical density in order to improve the aesthetic appearance (in particular, where the amount of antimicrobial metal is relatively low) and/or to produce a more uniform coating and/or to promote adhesion of the antimicrobial metal, etc. The intermediate layer preferably comprises aluminum (e.g., in the form of a thin aluminum metal film produced by deposition from the gas phase), but any other material(s) can be used as well as long as they are suitable for the desired purpose(s) and, in particular, do not interfere with the release of the antimicrobial metal and the antimicrobial activity thereof.

In a preferred embodiment of the composite of the present invention, the first layer of the composite is laminated to the second layer (preferably a liquid-absorbing layer such as, e.g., a nonwoven) by using meltable fibers under heat and pressure. Welding (e.g., ultrasonic welding) is an example of the various other techniques which may be employed for this purpose. In the case of spot-welding the bond between the first layer, e.g., a mesh, and the second layer, e.g., a liquid-absorbing nonwoven, tends to be relatively weak, wherefore a type of bonding with a larger contact area between these layers is preferred. Yet another non-limiting example of the techniques for bonding the first and second layers together is the use of adhesives. In this case, the utilized adhesive should not significantly interfere with the release of the antimicrobial metal (e.g., silver) or cause inconvenience to the user.

Preferably, the first layer of the composite of the present invention is bonded to the second layer by continuous bonding, e.g., substantially completely (as opposed to bonding in certain places only, like in the case of, e.g., spot-welding). Where the first layer is laminated to the second layer by using meltable fibers, a sufficient amount of meltable fibers should be used to ensure sufficient resistance against delamination.

The composite of the present invention (without any additional layers which may optionally be present, such as, e.g., a backing layer etc.) will preferably have an area weight (as determined according to DIN EN 29073-1) of at least about 50 g/m$^2$, e.g., at least about 80 g/m$^2$, and not more than about 300 g/m$^2$, e.g., not more than about 230 g/m$^2$, or not more than about 160 g/m$^2$. Also, the composite preferably has a thickness (as determined according to DIN EN 29073-2) which is not lower than about 0.4 mm, e.g., not lower than about 0.5 mm, and not higher than about 2.5 mm, e.g., not higher than about 1.4 mm. Furthermore, the composite will usually show a peeling or delamination strength (as determined according to DIN 53357) of at least about 0.05 N/cm, e.g., at least about 0.15 N/cm, and not higher than about 1.5 N/cm, e.g., not higher than about 0.8 N/cm. The minimum single value of the peeling strength (as determined according to DIN 53357) will usually not be lower than 0.05 N/cm. Additionally, the composite will usually show a maximum tensile strength (as determined according to DIN EN 29073-3) of from about 10 N/cm to about 40 N/cm. Furthermore, the 24-hour release of antimicrobial metal (e.g., silver) provided by the composite of the present invention (as determined according to the method described hereinbelow) preferably is at least about 0.05 mg/m$^2$, particularly, at least about 0.1 mg/m$^2$, but usually it will not be higher than about 3 mg/m$^2$, e.g., not higher than about 2 mg/m$^2$ of composite.

A wound covering article according to the present invention may, by way of non-limiting example, comprise the above composite and a cover or backing layer arranged on the second layer of the composite (e.g., directly bonded to the second layer or to any intermediate layer such as, e.g., a liquid-permeable layer which may optionally be present in a composite wherein the second layer is made of a liquid-absorbing material). The cover layer may comprise any material that is suitable for this purpose. Non-limiting examples of corresponding materials include a nonwoven (e.g., composed of polyester), a polyolefin (e.g. polyethylene) film and a combination thereof. The cover layer may carry an adhesive on the surface which is to come into contact with the second (or intermediate) layer and, optionally, also with the skin. Non-limiting examples of suitable adhesives are disclosed in, e.g., DE 27 43 979 C3. For example, commercially available pressure-sensitive or UV-curable adhesives based on acrylate or rubber may be used for this purpose. Preferable is the use of thermoplastic hot-melt adhesives based on natural and synthetic rubbers and other synthetic polymers such as, e.g., acrylates, methacrylates, polyurethanes, polyolefins, polyvinyl derivatives, polyesters and silicones. These adhesives may optionally contain additives such as, e.g., tackifying resins, softeners, stabilizers and other auxiliary agents. Subsequent cross-linking of the adhesive by UV or electron beam radiation may be advantageous.

Hot-melt adhesives based on block copolymers, in particular, are distinguished by their numerous varieties. By specifically lowering the glass transition temperature of the pressure-sensitive adhesive through selection of the appropriate tackifier, softener, the polymer molecule size and molecular weight distribution of the individual components, an appropriate adhesion to the skin is ensured also at critical locations of the human locomotive system.

It has surprisingly been found that, for example, a wound covering article which does not have the antimicrobial metal (e.g., silver) on the surface of a liquid-permeable layer which is to come into contact with the wound (i.e., not on an external surface thereof), but has the metal on the opposite surface of the layer, is capable of releasing a sufficient amount of the metal to give rise to an antimicrobial (disinfectant) effect when the article is in contact with a wound.

It is surprising that a wound covering article (e.g., a wound dressing) according to the present invention shows an antimicrobial activity, as demonstrated by release tests of dissolved silver, as well as by efficacy studies. These studies demonstrate a marked antibacterial activity against *Escherichia coli* and *Pseudomonas aeruginosa* and a somewhat lower activity against *Staphylococcus aureus* and *Enterococcus hirae*, in this order.

A composite according to the present invention is useful, in particular, as a wound dressing or wound covering such as a compress. Its use in skin care, e.g., as a cosmetic towelette or in baby care is advantageous as well, particularly, because the antimicrobial metal in elemental form does not directly contact the skin.

A composite of the present invention in the form of, e.g., a wound dressing or other wound covering material which comprises an antimicrobial metal such as silver shows many advantages, including the following:

upon contact of the silver layer with a wound fluid, silver (ions) is (are) released and exert(s) an antimicrobial effect, there is no direct abrasion or release of silver particles into the wound or onto the skin, which minimizes the risk of complications in wound healing or skin care,
where a mesh, perforated film or the like is provided as a cover layer over a textile material (as liquid-absorbing material) fibers from the textile material are prevented from being released into the wound and/or adhering to the wound.

Surprisingly, the structure according to the present invention can be realized without, or at least without substantial loss, of antimicrobial activity. In the case of silver, this activity is observed already with a very slight coating of silver, and a coating of preferably at least about 10 mg silver/m$^2$ is particularly preferred to ensure satisfactory antimicrobial activity. More silver can also be applied, e.g., for reasons of the manufacturing process. It has been shown, for example, that the application of as much as about 600 mg/m$^2$ of silver does not harm the user.

A comparison with known silver-containing wound dressings has shown that a dressing according to the present invention releases an advantageously high amount of silver at the beginning of the application. Moreover, the release rate is also sufficiently high over an extended period after application; excessive doping with silver is, therefore, not required, and the wound dressing does not have to be replaced already after a short period of time. This is of great advantage to users since they can use the dressing for longer periods without loss of antimicrobial (disinfecting) activity.

Another advantage of a dressing according to the present invention is related to abrasion. Rubbing one's finger on the side of the dressing which faces the skin reveals no abraded material, let alone black discoloration, in contrast to known wound dressings. This is particularly advantageous, in particular, for aesthetic reasons, for dressings that are used without a physician's supervision.

In addition to its use as a dressing or wound covering in the form of, e.g., a compress, the composite according to the present invention can also be used in other areas, e.g., for skin care applications. For example, moistened skin may be covered or wiped with the composite, for example in the form of a cloth. The moisture will penetrate the cover layer into the moisture-absorbing layer and thereby contact the metal (silver) layer. The antimicrobial metal will be released, thereby providing the antimicrobial effect associated with the metal. One of the advantages of the composite of the present invention is that the skin will not get discolored in these cosmetic uses. This is a substantial improvement over conventionally used products such as, e.g., baby care wipes and dressings.

Other exemplary embodiments and advantages of the present invention may be ascertained by reviewing the present disclosure and the accompanying drawing.

BRIEF DESCRIPTION OF THE DRAWINGS

The present invention is further described in the detailed description which follows, in reference to the noted plurality of drawings by way of non-limiting examples of exemplary embodiments of the present invention, in which like reference numerals represent similar parts throughout the several views of the drawings, and wherein:

FIG. 3 shows a top schematic view of an embodiment of the present invention in the form of a bandage product; and FIG. 4 shows a cross-sectional schematic view of an embodiment of the present invention in the form of a bandage product.

DETAILED DESCRIPTION OF THE PRESENT INVENTION

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show structural details of the present invention in more detail than is necessary for the fundamental understanding of the present invention, the description taken with the drawings making apparent to those skilled in the art how the several forms of the present invention may be embodied in practice.

Figure 1:
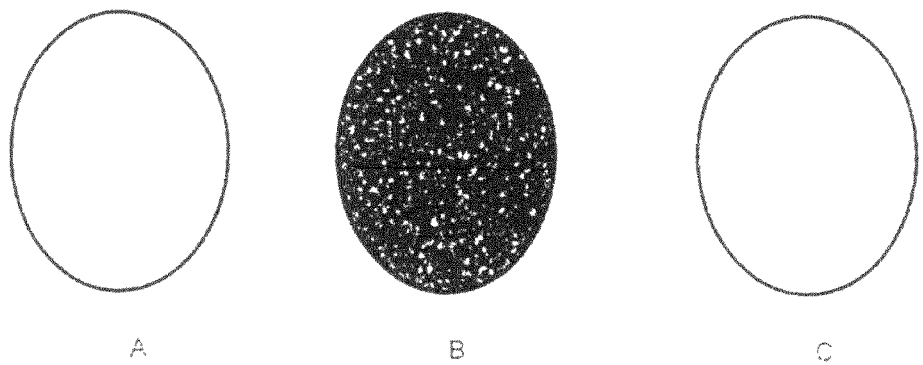
FIG. 1 shows the results of discoloration tests carried out with various wound dressings.

Abrasion resistance tests were used to examine abrasion resistance. These tests were analogous to the rubbing fastness test for dyes and prints according to DIN 54021. The subsequent evaluation was carried out according to ISO 105-A03: 1993 with a gray scale of from 1 to 5.1 represents a strong, black discoloration, and 5 represents no discoloration at all. The results are shown in FIG. 1, wherein the tested products are identified as follows:

A: Acticoat®; grayness: 3
   B: silver-coated dressing, silver facing the skin; grayness: 2
   C: dressing according to the invention, manufactured as described below; grayness: 5

The dressing according to the present invention (FIG. 1, C) has a grayness of 5, i.e., shows no discoloration. The comparative products, on the other hand, show discolorations with a grayness of 2 to 3. This advantageous reduction of abrasion in the case of the product of the invention is advantageous, especially, for aesthetic reasons.

Figure 2:
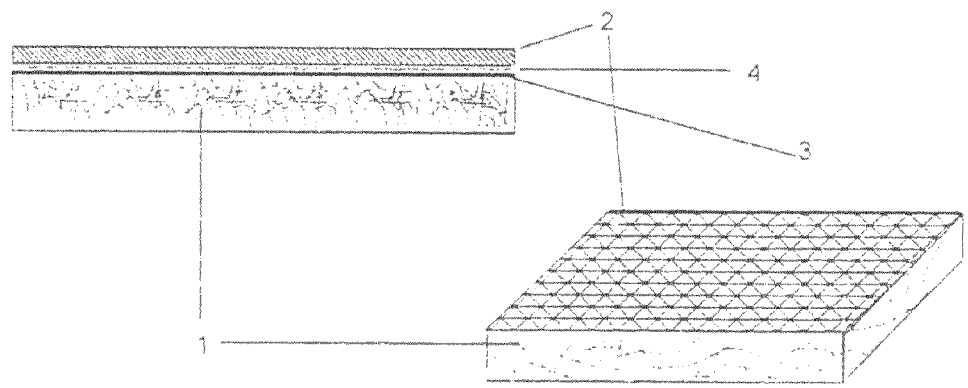
FIG. 2 shows top and cross-sectional schematic views of the general structure of an embodiment of the present invention.

FIG. 2 shows top and cross-sectional schematic views of the general structure of an embodiment of the composite according to the present invention. A liquid-permeable layer (2) is laminated onto a liquid-absorbing layer (1). On the side which faces layer (1), layer (2) is coated with silver (3). In a preferred embodiment, a layer of aluminum (4) is arranged between layer (1) and the silver coating (3). The aluminum layer makes it easier to coat the silver more uniformly and improves the appearance.

The composite according to the present invention is particularly suitable for use in, or as a wound dressing for self-adhesive bandage products, and also as an isolated wound covering that may be additionally fastened to the wound.

FIGS. 3 and 4 show top and cross-sectional schematic views of another embodiment of a material according to the present invention in the form of an adhesive strip. The dressing (A) which comprises the following layers:
   liquid-absorbing layer (1)
   liquid-permeable layer (2)
   aluminum layer (4)
   silver layer (3)
is provided on a backing layer (5) which is coated with an adhesive layer (6). The strip thus has a structure which is similar to that of classic bandages. Prior to use, the adhesive layer and the wound covering may be covered with a sealing paper (7).

Where additional adhesion is desired, the dressing according to the invention can be adhered to the skin by adding adhesive around the edge as shown in FIG. 3. In this case, the dressing according to the present invention will have a structure similar to that of known wound bandages. Peripheral adhesion is possible as in the case of bandages, as is adhesion on both sides as in the case of rolled stock.

The dressing material according to the present invention—with or without additional edge adhesive—may be placed on a wound in the usual way, with substantially no elemental silver coming into contact with the wound.

Once the silver-containing dressing is removed, the antibacterial effect ceases. Usually, the skin or wound will not have to be washed as no antiseptics and antibiotics will have to be removed.

EXAMPLE

A commercially available polyethylene net (Delnet®, available from Applied Extrusion Technologies, and also available from Smith & Nephew Extruded Films Ltd. U.K.), having triangle-shaped holes (length of longest bisector: 400-700 μm) is coated, by vapor deposition, first with aluminum and then with silver (alternatively, a commercially available PE net that already is coated with aluminum may be used). The area weight of the resultant Al and Ag coated net is about 20 g/m$^2$. The content of Al is about 60-80 mg/m$^2$ and the content of Ag is about 60-460 mg/m². The coated net is laminated to a needle-punched nonwoven (Malivlies) with the coated side facing the nonwoven. The nonwoven is composed of about 75 weight-% of rayon (viscose) and about 25 weight-% of polyethylene/polypropylene fibers and has an area weight of about 120 g/m². Lamination is carried out under heat and pressure (by slightly melting the PE/PP fibers and pressing the two layers together).

A material which was made as described above showed the following properties:
Area weight (DIN EN 29073-1): 125 g/m²
Thickness (DIN EN 29073-2): 0.75 mm
Maximum tensile strength (DIN EN 29073-3): 15.8 N/cm
Delamination/peeling strength (DIN 53357): 0.95 N/cm
Minimum single value of delamination/peeling strength (DIN 53357): 0.40 N/cm
Liquid absorption (DIN 53923): 620 g/m²
Release of silver (see the method described below): 0.46 mg/l after 24 h
Efficacy: The antimicrobial activity against *Staphylococcus aureus, Enterococcus hirae, Escherichia coli, Pseudomonas aeruginosa* and *Candida albicans* was tested. It was found that in all cases the material showed bactericidal, bacteriostatic and/or fungicidal activity.

Method of Determining Release of Silver:

The release of silver was determined by an extraction of the silver from a sample of the material (square with a side of 30+/−1 cm) into a phosphate-buffered saline solution (15 ml of PBS solution) at 31° C. for 24 h. The PBS solution is described by Dulbecco (John Paul, "Zell-und Gewebekulturen", Walter de Gruyter Publishers, 1980, p. 92). The content of Ca and Mg ions was adjusted to wound fluid levels (0.19 g/L of $CaCl_2 \times 2H_2O$; 0.27 g/L of $MgSO_4 \times 7H_2O$; Geigy Scientific Tables, Vol. 3, Ciba-Geigy Ltd., 8th Ed. 1984, p 82). Following the extraction, the sample was carefully removed from the solution. The aqueous phase was acidified and the silver concentration was determined by atomic absorption spectroscopy using an $air/C_2H_2$ flame at a wavelength of 328.1 nm.

It is noted that the foregoing examples have been provided merely for the purpose of explanation and are in no way to be construed as limiting of the present invention. While the present invention has been described with reference to an exemplary embodiment, it is understood that the words which have been used herein are words of description and illustration, rather than words of limitation. Changes may be made, within the purview of the appended claims, as presently stated and as amended, without departing from the scope and spirit of the present invention in its aspects. Although the present invention has been described herein with reference to particular means, materials and embodiments, the present invention is not intended to be limited to the particulars disclosed herein; rather, the present invention extends to all functionally equivalent structures, methods and uses, such as are within the scope of the appended claims.

What is claimed is:

1. An antimicrobial composite, wherein the composite comprises a first, liquid-permeable layer which is a polyethylene mesh that has openings having a size of from about 400 µm to about 700 µm to provide an open area of from about 15% to about 60% of a surface area of the first layer, which mesh is substantially completely laminated to a second liquid-absorbing layer having a liquid-absorbing capacity of at least about 400 g/m² to provide a peeling strength between the first layer and the second layer of at least about 0.15 N/cm, which mesh comprises a coating of not more than about 80 mg/m² silver as such on a side which faces the second layer, and wherein substantially no silver in elemental form is present on exterior surfaces of the composite, and the composite shows a 24-hour release of silver of at least about 0.1 mg/m².

2. The composite of claim 1, wherein an aluminum coating is arranged between the silver coating and the first layer.

3. The composite of claim 1, wherein the second layer comprises a superabsorbent in an amount of from about 0.01% to about 40% by weight, based on the second layer.

4. The composite of claim 1, wherein the silver is present in an amount of at least about 50 mg/m².

5. The composite of claim 1, wherein the composite has a peeling strength between the first layer and the second layer of up to about 1.5 N/cm.

6. The composite of claim 1, wherein the composite shows a maximum tensile strength of from about 10 N/cm to about 40 N/cm.

7. The composite of claim 1, wherein the second layer comprises a nonwoven which comprises at least one of polyethylene, polypropylene, polyester, and viscose.

8. The composite of claim 1, wherein the openings have a substantially triangular shape.

9. The composite of claim 1, wherein the first layer has a thickness of from about 0.02 mm to about 0.8 mm.

10. The composite of claim 1, wherein the first layer has a thickness of from about 0.05 mm to about 0.5 mm.

11. The composite of claim 1, wherein the second layer has a thickness of from about 0.02 mm to about 2.5 mm.

12. The composite of claim 10, wherein the second layer has a thickness of from about 0.5 mm to about 1.4 mm.

13. The composite of claim 1, wherein the second layer has a liquid-absorbing capacity of up to about 1000 g/m².

14. The composite of claim 1, wherein the second layer has an area weight of from about 80 g/m² to about 200 g/m².

15. The composite of claim 1, wherein the second layer comprises a superabsorber.

16. The composite of claim 15, wherein the superabsorber comprises a polymer having recurring units derived from acrylic acid and derivatives thereof.

17. The composite of claim 16, wherein the superabsorber is present in an amount of from 0.01% to about 40% by weight, based on a weight of the second layer.

18. The composite of claim 2, wherein the first layer is coated with aluminum on one side thereof.

19. The composite of claim 1, wherein the composite has an area weight of from about 80 g/m² to about 160 g/m².

20. The composite of claim 1, wherein the composite has a thickness of from about 0.4 mm to about 1.4 mm.

* * * * *